United States Patent [19]
Girard et al.

[11] Patent Number: 6,082,398
[45] Date of Patent: *Jul. 4, 2000

[54] DEVICE FOR REGULATING THE FLOW OF GASES HAVING SUBSTANTIALLY DIFFERENT MOLAR MASSES

[75] Inventors: Jean-Marc Girard, Paris; Alain Mail, Domene; Yves Marot, Buc, all of France

[73] Assignee: L'Air Liquide, Societe Anonyme pour l'Etude et l'Exploitation des Procedes Georges Claude, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/752,072

[22] Filed: Nov. 19, 1996

[30] Foreign Application Priority Data

Nov. 5, 1996 [FR] France ................... 96 13434

[51] Int. Cl.$^7$ ........................................ F17D 1/02
[52] U.S. Cl. .............. 137/599; 137/599.1; 137/863; 137/872; 137/605; 251/331
[58] Field of Search ............................ 137/605, 599, 137/599.1, 872, 597, 863; 251/331

[56] References Cited

U.S. PATENT DOCUMENTS

| | | | |
|---|---|---|---|
| 2,169,043 | 8/1939 | Goehring | 137/872 |
| 3,038,449 | 6/1962 | Murphy | 137/599 |
| 3,104,823 | 9/1963 | Hayes | 137/599.1 |
| 3,181,797 | 5/1965 | Hayes | 137/599.1 |
| 3,792,719 | 2/1974 | Dickinson | 137/599 |
| 3,830,256 | 8/1974 | Cox | 137/599 |
| 3,905,394 | 9/1975 | Jerde . | |
| 3,941,144 | 3/1976 | Cornil | 137/599.1 |
| 4,030,523 | 6/1977 | Cram | 137/599 |
| 4,192,346 | 3/1980 | Iizumi | 137/599 |
| 4,644,967 | 2/1987 | Wyatt | 137/599 |
| 4,706,492 | 11/1987 | Jones, Jr. et al. . | |
| 4,977,929 | 12/1990 | Chinnock | 251/331 |
| 5,275,201 | 1/1994 | Zimmerly | 137/597 |
| 5,333,643 | 8/1994 | Gilchrist | 137/605 |
| 5,419,924 | 5/1995 | Nagashima | 137/605 |

FOREIGN PATENT DOCUMENTS

| | | |
|---|---|---|
| 0 479 633A1 | 4/1992 | European Pat. Off. . |
| 2 093 653 | 1/1972 | France . |
| 93 03 693 | 6/1993 | Germany . |

*Primary Examiner*—Denise L. Ferensic
*Assistant Examiner*—Joanne Y. Kim
*Attorney, Agent, or Firm*—Burns, Doane, Swecker & Mathis, L.L.P.

[57] ABSTRACT

A device for regulating the flow of gases having substantially different molar masses, comprising an always-open feed line connected to a gas source at a defined pressure and to an apparatus a first calibrated restriction placed in the feed line, a bypass line connected via at least one of its two ends to a valve of a branching valve or a 4-way valve, placed in the feed line, and via the other end to a point of connection to the feed line, the valve being switchable between a first position for bringing the feed line into communication with the bypass line and a second position for isolating the bypass line from the feed line, and a second calibrated restriction placed in the bypass line, the first calibrated restriction being placed on the feed line portion lying between the valve and the point of connection.

14 Claims, 4 Drawing Sheets

US 6,082,398

DEVICE FOR REGULATING THE FLOW OF GASES HAVING SUBSTANTIALLY DIFFERENT MOLAR MASSES

BACKGROUND OF THE INVENTION (i) Field of the Invention

The invention relates to a device for regulating the flow of gases having substantially different molar masses.

(ii) Description of Related Art

In the field of the analysis of very-high purity gases, it is increasingly necessary to analyze sequentially various kinds of gases using the same analyzer, such as a trace-impurity analyzer like an atmospheric-pressure ionization mass spectrometer.

In order to ensure that the analyzer operates optimally, it is necessary to set the volume flow rate of the gas introduced into the analyzer at an approximately constant value irrespective of the gas to be analyzed.

In order not to contaminate the gas to be analyzed, calibrated orifices are used for regulating the gas flow rate, these orifices being mounted in a line for delivering gas to the analyzer. In the sonic regime, in which the pressure upstream of the orifice is at least twice as high as the pressure downstream of the orifice, controlling the pressure upstream of the orifice enables the flow of gas into the delivery line to be controlled within a certain range.

Nevertheless, regulating a gas flow using a calibrated orifice poses a problem in the case in which the gases to be analyzed have substantially different molar masses, such as, for example, hydrogen and nitrogen, since the volume flow rate is, for the same upstream pressure, proportional to $M^{-\frac{1}{2}}$, where M is the molar mass of the gas.

In this case, the volume flow rate of hydrogen through a calibrated orifice is, for the same upstream pressure, approximately four times greater than the flow rate of nitrogen.

A large variation in the pressure upstream of the orifice in order to obtain the optimum flow rate is in most cases not possible for technical reasons. Either the plant cannot withstand the high pressure necessary for obtaining the same optimum flow rate for a gas of greater molar mass, in the case in which the orifice is designed for an optimum flow rate of a gas having a low molar mass, or, in the opposite case, the necessary upstream pressure is so low that sonic conditions, necessary for regulating the flow rate, are no longer guaranteed.

Consequently, an optimum flow rate of gas to be delivered to the analyzer can no longer be guaranteed without changing the pressure upstream of the orifice in significant amounts.

In addition, such large variations in the upstream pressure must be avoided in the field of the analysis of very-high purity gases, since these variations lead to transient regimes during which any surface in contact with the gas is likely to desorb and adsorb molecules, a process likely to modify the composition of the gases flowing in the lines.

A problem, similar to the one raised above, occurs for dilution units used with gases of substantially different molar mass.

A device designed for the feed of an analyzer having very high sensitivity is known from document FR-A-2714968 in the name of the Applicant Company. This device includes means for splitting an overall flow of a source of pure gas in order to feed various stages of a dilution unit with a precise partial flow. This flow splitting is produced using two bypassed lines connected in parallel to a line for sampling the pure gas. A calibrated orifice is placed at the inlet of each bypassed line and a flow regulator is placed in the sampling line in order to impose the overall flow rate feeding the dilution unit.

With an imposed volume flow rate, the pressure upstream of the orifice is proportional to $M^{+\frac{1}{2}}$, where M is the molar mass of the gas flowing through the restriction. It is therefore understood that, at an imposed volume flow rate, the upstream pressure in the case of a light gas such as hydrogen is approximately four times lower than that in the case of nitrogen.

If the orifices for the flow splitting are therefore designed for a gas of high molar mass, it is no longer possible to guarantee the sonic conditions, or barely so, when the same flow-splitting means are used with a light gas. However, for precise regulation of the flow, it is absolutely essential to satisfy the conditions of a sonic or near-sonic regime. In this case too, the problem occurs of transient regimes affecting the composition of the gases in the lines.

SUMMARY AND OBJECTS OF THE INVENTION

The present invention aims to solve the problems associated with very different molar masses of the gases treated, by providing a regulating device which allows regulation, based on a known upstream pressure, for gases having substantially different molar masses and which does not lead to significant transient flow-rate or pressure regimes in the lines.

For this purpose, the subject of the invention is a device for regulating the flow of gases having substantially different molar masses, comprising an always-open feed line connected, on the one hand, to a known source of pressurized gas and, on the other hand, to an apparatus, and a first calibrated restriction placed in the feed line, characterized in that it furthermore comprises, on the one hand, a bypass line connected via at least one of its ends to a valve of the branching valve or 4-way valve type, placed in the feed line, and via the other end to a point of connection to the feed line, said valve being switchable between a first position for bringing the feed line into communication with the bypass line and a second position for isolating the bypass line from the feed line and, on the other hand, a second calibrated restriction placed in the bypass line, the first calibrated restriction being placed on the feed line portion lying between the valve and the point of connection.

The device according to the invention may include one or more of the following characteristics:

a) the second calibrated restriction is placed close to the downstream end of the bypass line;

b) the calibrated restrictions are calibrated orifices;

c) the valve used is of the "4-way valve" type, lying at the downstream end of the bypass line (downstream point of connection between the feed and bypass lines), the first calibrated restriction then lying on the feed line portion between the upstream point of connection of the bypass line and the valve, upstream of this valve. It is then advantageous to place on the "fourth" way, which may be termed the "leakage way", an additional calibrated restriction, the diameter of which is slightly greater than that of the first and second restrictions, thus making it possible to maintain a small leakage flow in this line.

The detailed operation of such a configuration will be described later within the context of the figures;

d) the valve used is of the branching valve type, lying at the upstream point of connection or at the downstream point of connection of the bypass line to the feed line, the first calibrated restriction then lying, depending on the case, upstream or downstream of the valve;

e) two branching valves are used, one at each point of connection of the bypass line to the feed line, the first calibrated restriction then lying on the feed line portion between the two valves;

f) the branching valve comprises a first conduit permanently connected via a first end to the bypass line, a second conduit placed in the feed line, and an actuator which can be switched between a position for bringing the first conduit into communication with the second conduit and a position for isolating the first conduit from the second conduit, the second conduit being free of flow-stagnation volumes;

g) the second conduit of the valve includes a chamber in which the second end of the first conduit emerges and the valve includes a closure element which is acted upon by the actuator of the valve, which closure element closes off, in said isolating position, the end of the first conduit emerging in said chamber and which is set back with respect to this end of the first conduit in said communicating position;

h) the end of the first conduit emerging in said chamber is provided with a seal projecting into the chamber, the closure element comprises an elastically deformable diaphragm forming part of the wall of the chamber opposite the seal, the diaphragm being pressed in a sealed manner onto the seal against the spring force of the diaphragm, in said isolating position, by a pusher of the actuator;

i) the valve includes means for controlling the switching of the actuator between said communicating and isolating positions.

BRIEF DESCRIPTION OF THE DRAWINGS

Other characteristics and advantages of the invention will appear from the following description given by way of example but having limiting character, with regard to the appended drawings in which.

DETAILED DESCRIPTION OF PREFERRED EMBODIMENTS

Figure 1:
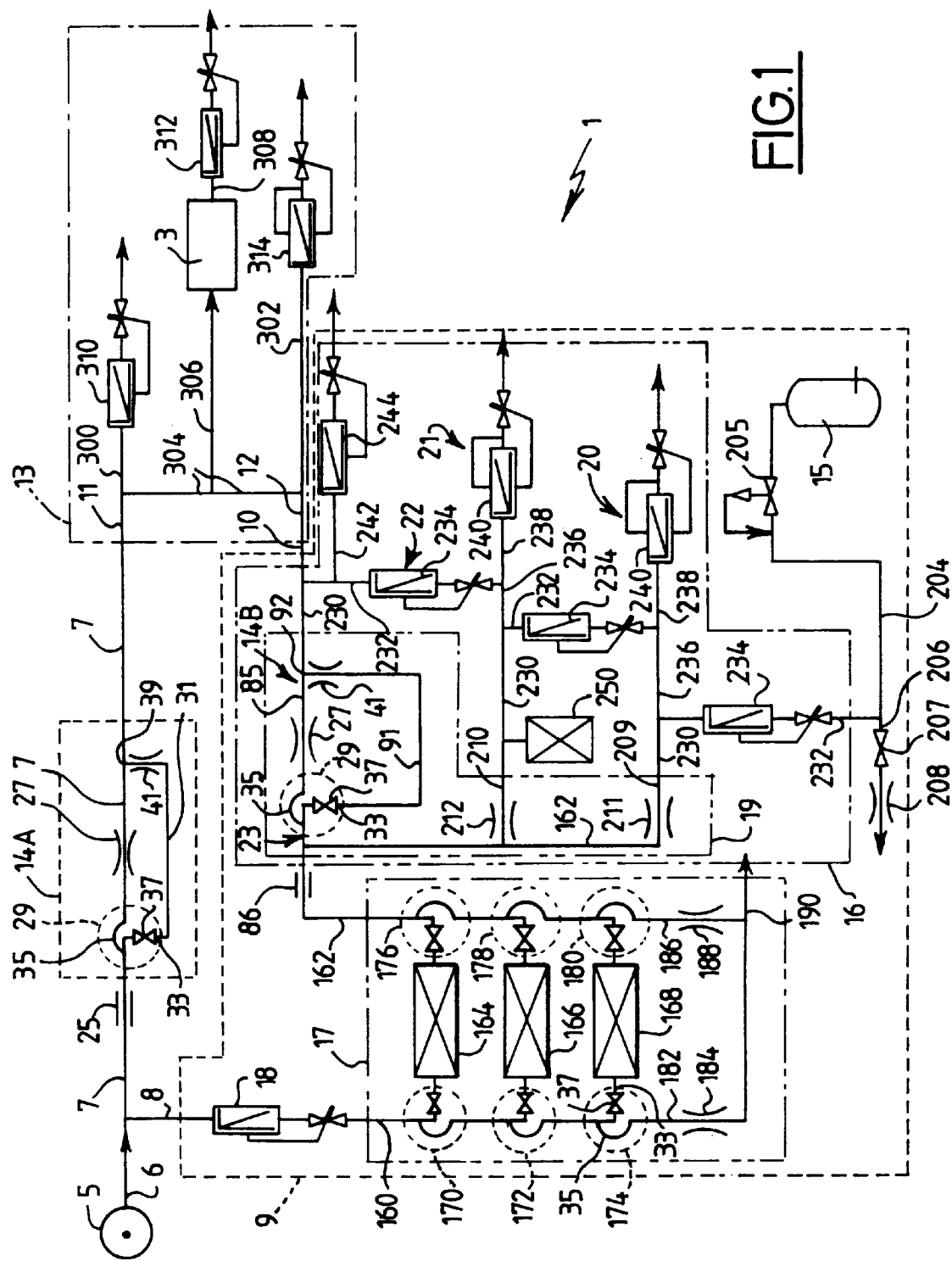
FIG. 1 is a general diagram of a plant for delivering, to an apparatus, either a gas to be analyzed or a pure gas, or else a gas charged with a predetermined quantity of impurities.

FIG. 1 shows a plant 1 for delivering gas to an apparatus 3 such as, for example, an apparatus for analyzing trace impurities in a gas, of the atmospheric-pressure ionization mass spectrometer. Such an analyzer 3 is capable of measuring trace impurities in a gas at very low concentrations of between $10^{-2}$ to $10^{-5}$ ppm, or indeed from to $10^{-3}$ to $10^{-6}$ ppm. As will be explained in detail hereinbelow, this plant 1 delivers, to the apparatus 3, alternately a pure reference gas or "zero gas", that is to say a gas typically containing less than $10^{-5}$ ppm of impurities, a gas charged with a predetermined quantity of known gaseous impurities such as, for example, $H_2O$, $CO_2$, $CO$, $O_2$, $CH_4$, $H_2$, etc., at concentrations varying within a range extending from $10^{-5}$ ppm to $10^{-2}$ ppm, or else a gas to be analyzed. Furthermore, this plant must control the parameters relating to the introduction of the gas into the analyzer 3, such as the pressure and flow rate.

In addition, this plant must allow the successive use of various kinds of gas to be analyzed.

For this purpose, a source 5 of a pressurized gas to be analyzed is connected via a sampling line 6 to the gas delivery plant 1. This source 5 comprises, for example, a single source of one kind of gas to be analyzed, or several pressurized sources of various kinds of gases, each connected via a sampling line to a device intended to deliver any one of several gases to an apparatus, such as the device described in French Patent Application No. FR-960756096 filed in the name of the Applicant Company on Jun. 18, 1996.

The sampling line 6 is connected, on the one hand, to an analyzing line 7 and on the other hand, to a feed line 8 of a device 9 for delivering a pure gas or a gas charged with a predetermined quantity of gaseous impurities.

The analyzing line 7 and an outlet line 10 of the delivery device 9 are each connected to a corresponding inlet line 11, 12 of a selection device 13 in order to deliver to the apparatus 3 either the gas contained in the analyzing line 7 or the gas output by the outlet line of the delivery device 9.

A device 14A, for regulating a predetermined gas flow for gases to be analyzed that have substantially different molar masses, is placed in the analyzing line 7.

The delivery device 9 comprises a source of pure gas, a source 15 of impurities and means 16 of diluting the impurities in the pure gas in a predetermined manner.

The source of pure gas consists, on the one hand, of the source 5 of the gas to be analyzed and, on the other hand, of a unit 17 for purifying the gas output by the source 5, the flow of gas feeding the purification unit being controlled by means of a mass flow regulator 18 placed in the feed line 8.

It is observed that the purification unit is advantageously downstream of the flow regulation.

The diluting means 16 include means 19 of splitting the gas flow output by the purification unit 17, which means feed several dilution stages 20, 21, 22 placed in series.

A branch 23 of the flow-splitting means 19 includes a device 14B for regulating a predetermined upstream gas pressure for gases having substantially different molar masses, the structure of this device 14B being identical to that of the regulating device 14A.

The structure and operation of the various units of the gas delivery plant 1 will be described in detail hereinbelow.

I. Device for regulating the flow of gases having substantially different molar masses.

I.1. Structure of the regulating device

The regulating device 14A is placed in the analyzing line 7. Placed upstream of this regulating device 14A is a pressure gauge 25 for determining the pressure upstream of the regulating device 14A.

The regulating device 14A includes, for the embodiment shown, (other embodiments will indeed be illustrated within the context of FIGS. 5) a calibrated restriction 27, for example a calibrated orifice, placed in the analyzing line 7. Placed upstream of the orifice 27 is a branching valve 29, shown diagrammatically surrounded by dashes, for the selective use of a bypass line 31.

The valve 29 comprises a first conduit 33 permanently connected via one end to the bypass line 31. It furthermore comprises a second, always-open conduit 35 which is placed in the analyzing line 7.

The first conduit 33 and the second conduit 35 of the valve 29 may be brought into communication by an actuator 37, as will be explained in detail hereinbelow, which can switch between a position for bringing the first conduit 33 into communication with the second conduit 35 and a position for isolating the first conduit 33 from the second conduit 35. The bypass line 31 is connected via its other end 39, downstream of the orifice 27, to the analyzing line 7.

A second calibrated orifice 41 is advantageously placed in the bypass line 31, as close as possible to the end 39 of the latter. Thus, a flow-stagnation volume, formed in the isolating position of the two conduits 33 and 35 by that part of the bypass line 31 lying between the orifice 41 and the end 39, is as small as possible.

The structure of the regulating device 14B for this embodiment is identical to that of the device 14A. This is why the identical elements bear the same reference numbers.

This device thus includes a first orifice 27 placed in a feed line 85 for a pure gas output by the purification unit 17. Placed in this line 85 is a branching valve 29 identical to that of the device 14A. Connected to the conduit 33 of the valve 29 is one end of a bypass line 91. The other end of this line 91 is joined downstream of the orifice 27 to the feed line 85. A calibrated orifice 41 is placed as close as possible to the end 92 via which the bypass line 91 is joined to the feed line 85.

I.2. Structure of a branching valve of the regulating devices

An embodiment example of the valve 29 fitted in the regulating devices 14A and 14B is described in detail hereinbelow. Such a valve, of the electropolished DAD type, is for example derived from a valve marketed by the company NUPRO and manufactured by the company SWAGELOK.

Figure 3:
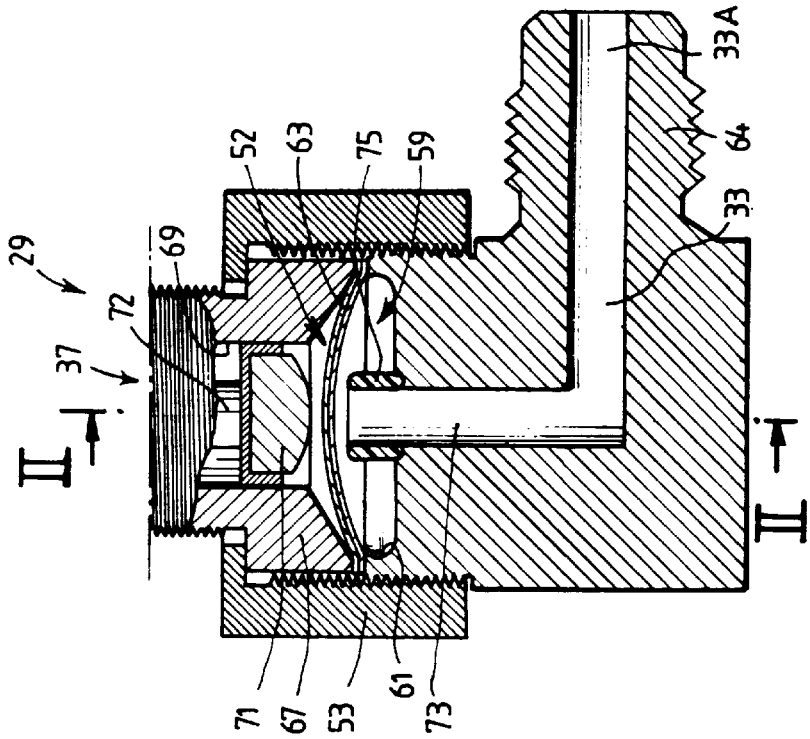
FIG. 3 is a sectional view, along the line III/III in FIG. 2, of the same valve in the communicating position.
Figure 2:
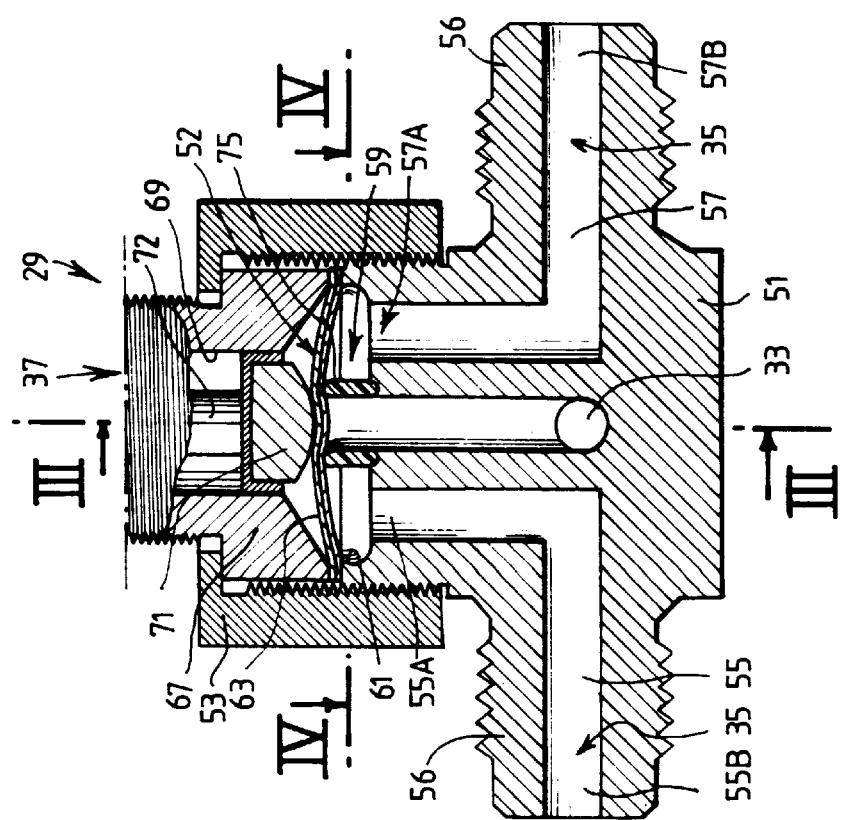
FIG. 2 is a sectional view along the line II/II in FIG. 3 of a branching valve of the regulating device in FIG. 1 as well as of a valve of a purification unit in FIG. 1, in the isolating position.

As shown in FIGS. 2 and 3, the valve 29 includes a body 51, in which the first conduit 33 and the second conduit 35 are made, a closure member 52 and an actuator 37, shown in part, which is screwed onto the body 51 by means of a nut 53.

The second conduit 35 (FIG. 2) is formed by two conduit sections 55 and 57 and by an axisymmetric annular chamber 59. Emerging in a lateral part of the bottom of this chamber 59 is one 55A, 57A of the two ends of each conduit section 55, 57.

The other end, 55B, 57B of each conduit section 55, 57 emerges in a respective lateral connector 56 on the body 51. These ends 55B and 57B are diametrically opposed. The two connectors 56 are intended to be connected to the analyzing line 7, with regard to the regulating device 14A and to the feed line 85, with regard to the regulating device 14B.

The chamber 59 is formed by a substantially cylindrical recess 61, made in the upper face of the body 51, and by the closure member 52. This closure member itself consists of a combination of two diaphragms 63 joined together, these diaphragms covering the recess 61 and constituting the upper wall of the chamber 59.

The diaphragms 63 are made of an elastically deformable material, for example metal. Each diaphragm 63 is a disc, the central part of which is domed in a direction away from the body 51. The edge of the diaphragms 63 is clamped in a sealed manner between the annular edge of the recess 61 and an annular edge of a holding piece 67 which forms part of the actuator 37. The piece 67 is made in the form of a dish so as to allow movement of the domed part of the diaphragms 63.

In its central part, opposite the diaphragms 63, the holding piece 67 includes a guide bore 69 in which a pusher 71 driven by a rod 72 of the actuator 37 can slide.

The first conduit 33 of the valve 29 comprises a single straight blind hole, which extends perpendicularly to the axis defined by the ends 55B, 57B of the conduit sections 55, 57, and a connecting duct 73 which emerges at the center of the recess 61.

One end, 33A, of the first conduit 33 emerges in a respective lateral connector 64 on the body 51 and is intended to be connected to the bypass line 31 in the case of the device 14A or to the bypass line 91 in the case of the device 14B.

The end of the duct 73 emerging in the recess 61 includes a cylindrical seal 75 which is forcibly fitted into the body 51 of the valve and which projects into the chamber 59.

Figure 4A:
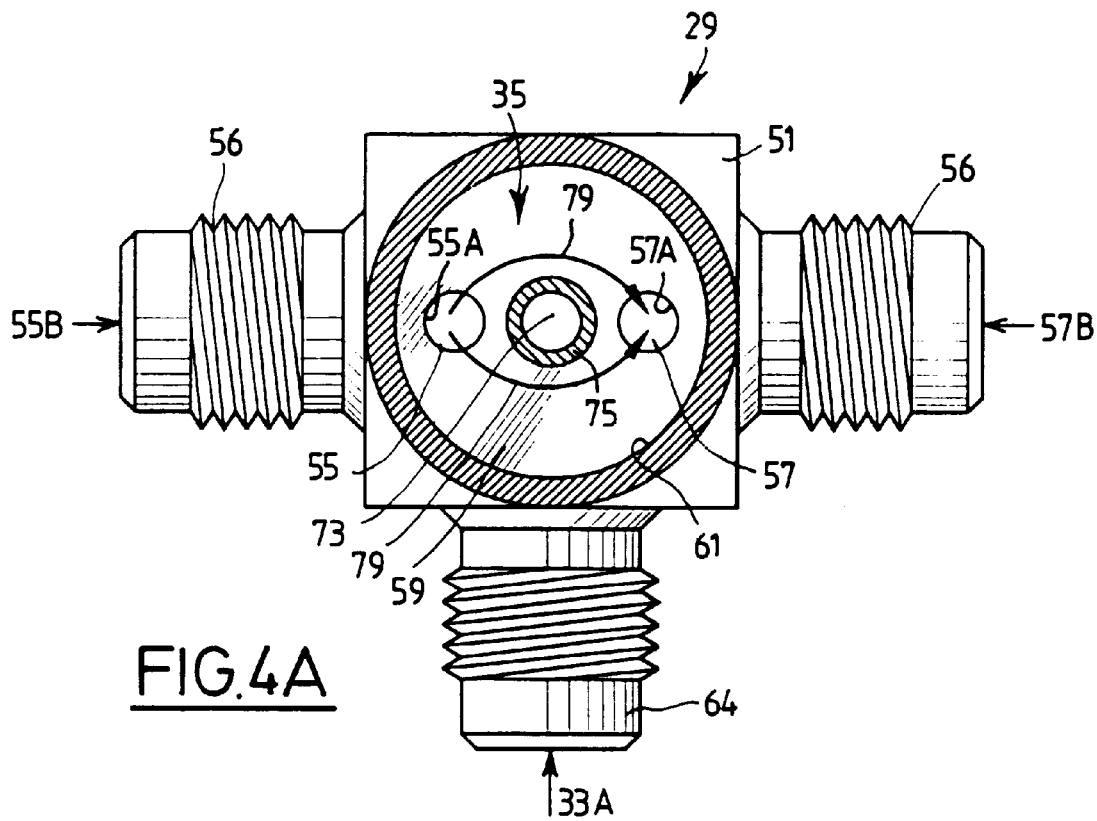
FIG. 4A is a sectional view, along the line IV/IV in FIG. 2, of the valve in the isolating position.

FIGS. 2 and 4A show the valve 29 in the position for isolating the first conduit 33 from the second conduit 35. In such a case, the central part of the diaphragms 63 is pressed in a sealed manner by the pusher 71 onto the seal 75 so that the duct 73 is isolated from the chamber 59.

Nevertheless, a gas introduced into the second conduit 35 of the valve flows freely, for example from the conduit section 55 into the chamber 59 and then into the conduit section 57, as shown by the arrows 79 in FIG. 4A. It is clear that the second conduit 35 of the valve thus formed has no flow-stagnation volume.

Figure 4B:
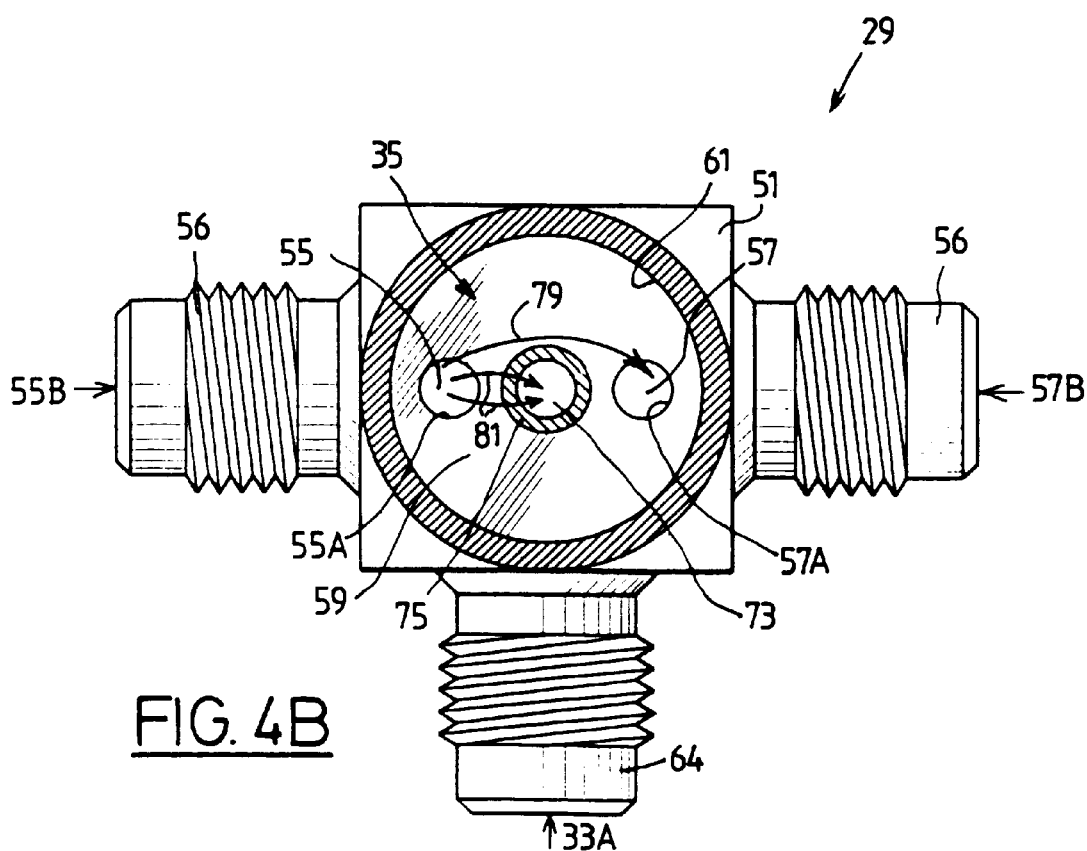
FIG. 4B is a sectional view, along the line IV/IV in FIG. 2, of the valve in the communicating position.

FIG. 3 and FIG. 4B correspond to a position for bringing the first conduit 33 into communication with the second conduit 35. In such a case, the pusher 71 is set back. The diaphragms 63 resume their initial domed shape by virtue of their spring force. Consequently, a free space is formed between the diaphragms 63 and the seal 75 so that the gas flowing in the second conduit 35 flows away largely via the duct 73 into the first conduit 33, as shown by the arrows 81 in FIG. 4B.

I.3. Operation of the regulating device

The operation of the regulating devices 14A, 14B are explained hereinbelow with regard to FIG. 1. For this purpose, two operating methods will be distinguished.

In a first operating mode, the pressure upstream of the regulating device is imposed and the flow rate must be approximately the same for two gases having substantially different molar masses. This operating mode corresponds to the device 14A placed in the analyzing line 7.

In a second operating mode, the gas flow rate upstream of the regulating device is imposed and it is desired to establish a sonic flora regime. This operating mode corresponds to that produced by the regulating device 14B.

I.3.1. Imposed pressure operation

For a light gas, such as hydrogen for example, the valve 29 of the regulating device 14A is switched into the position for isolating the first conduit 33 from the second conduit 35. The gas from the source 5 flows freely in the analyzing line 7 through the second conduit 35 and the orifice 27. In the case of a flow in sonic regime, that is to say in the case in which the ratio between the pressure upstream of the orifice 27 and the pressure downstream of this orifice is greater than 2, it is known that the volume flow rate $D_{27}$ of the gas through the orifice 27 is equal to:

$$D_{27}=K \times P \times S_{27} \times M^{-\frac{1}{2}}$$

where;

P=pressure upstream of the orifice 27, $S_{27}$=cross section of the orifice 27, M=molar mass of the gas flowing through the orifice, and K=constant which depends on the temperature and nature of the gases.

By virtue of the fact that the conduit 35 of the valve 29 has no flow-stagnation volume and that the orifice 41 of the bypass line 31 is placed close to the end 39 of this line, the regulating device 14A introduces only a negligible flow-stagnation volume into the analyzing line 7 in the position for isolating the first conduit 33 from the second conduit 35 of the valve.

In the case of a gas having a greater molar mass, such as $N_2$ for example, for the same pressure the flow rate through the orifice 27 falls proportionally to the square root of the ratio of the molar masses of the two gases, for example in the case of $N_2$ and $H_2$, to approximately one quarter of the flow rate obtained in the case of $H_2$. In this case, in order to maintain the flow rate delivered by the analyzing line 7 at approximately the same level as the flow rate of a gas of low molar mass, the valve 29 is switched to the state for bringing the first conduit 33 into communication with the second conduit 35. The gas then flows not only through the orifice 27 but also into the bypass line 31 through the orifice 41.

To the flow rate $D_{27}$ is then added, at the connection of the analyzing line 7 and the bypass line 31, the flow rate $D_{41}$ which is given, in sonic regime, by the equation:

$$D_{41}=K \times P \times S_{41} \times M^{-\frac{1}{2}}$$

The nomenclature used is analogous to that used for the flow rate $D_{27}$.

In order for the flow rate controlled by the regulating device 14A to be approximately equal in the case of two gases having respectively a molar mass $M_1$ and $M_2$, the cross section $S_{41}$ of the orifice 41 is chosen in such a way that it satisfies the equation:

$$S_{41}=((M_1^{1/2}/M_2^{1/2}) \times S_{27})-S_{27}$$

where $M_1$ is the molar mass of a gas having a high molar mass, and $M_2$ is the molar mass of a gas having a low molar mass.

Preferably, the cross section $S_{41}$ of the orifice 41 is chosen in such a way that the flow rate of $H_2$ in the isolating state of the valve 29 is comparable to the flow rate of $N_2$ through the orifice 27 and the orifice 41 in the communicating state of the valve 29.

I.3.2. Imposed-flow-rate operation

This operating mode of the regulating device is beneficial in the case in which the flow rate upstream of the regulating device is imposed and in which it is necessary to establish a sonic regime or a near-sonic regime for flow-regulating orifices, such as, for example, those of the flow-splitting means 19. The gas flow rate upstream of the regulating device 14B is imposed by the flow regulator 18.

It will be understood here that the "sonic" regime is preferred and that the fact of departing too far therefrom quite simply makes it difficult to calculate the flow distribution. It is therefore a question of finding a ratio of the upstream and downstream flow rates lying between 1.5 and 30.

In order to explain the imposed-flow-rate operation, it will be assumed that only the regulating device 14B alone placed in the feed line 85, as was described with regard to the device 14A. In the case in which the device 14B is placed in the flow-splitting means 19, the reasoning presented above applies correspondingly.

With a volume flow rate imposed, the pressure upstream of the orifice 27 in the isolating position of the valve 29 is given by the equation:

$$P=K' \times D_{18} \times M^{1/2} \times S_{83}^{-1}$$

with:

$D_{19}$=volume flow rate imposed by the flow regulator 18,

K'=a constant which depends on the nature of the gas and on the temperature, $S_{27}$=the cross section of the orifice 27.

The cross section of the orifice 27 is dimensioned in such a way that, for a light gas such as $H_2$, sonic conditions are attained upstream of the orifice 27.

In the case of a gas, such as $N_2$, having a high molar mass, the pressure upstream of the orifice 27, for the same flow rate, is approximately four times greater compared to the upstream pressure obtained in the case of $H_2$.

This is why the valve 29 is switched to the state for bringing the first conduit 33 into communication with the second conduit 35. The gas then flows not only through the orifice 27 but also through the orifice 41. The pressure upstream of the orifice 27 and of the orifice 41 is given by the equation $$P=K' \times D_{18} \times M^{1/2} \times (S_{27}+S_{41})^{-1}$$

with:

$S_{41}$=cross section of the orifice 41.

In order for the pressure upstream of the regulating device 14B to attain sonic conditions for two gases of different molar mass, the cross section $S_{41}$ of the orifice 41 is chosen in such a way that it satisfies the equation $$S_{41}=((M_1^{1/2}/M_2^{1/2}) \times S_{27})-S_{27}$$

where $M_1$ is the molar mass of a gas of high molar mass and $M_2$ is the molar mass of a gas having a low molar mass.

Of course, instead of the orifices 27 and 41 it is possible to use any calibrated restrictions, such as, for example, capillaries, or frits.

Moreover, provision may be made to use diaphragm valves 29 which include means for driving the actuator 37 between the communicating and isolating positions, such as pneumatic valves or electromagnetically-operated valves. The means for controlling the movement of the actuator of the valve are then connected to a control unit, such as a microcomputer or a controller, for example.

Figure 5A:
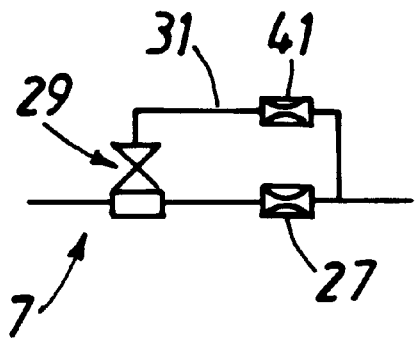
FIGS. 5A, 5B and 5C illustrate embodiments of the regulating device according to the invention.
Figure 5B:
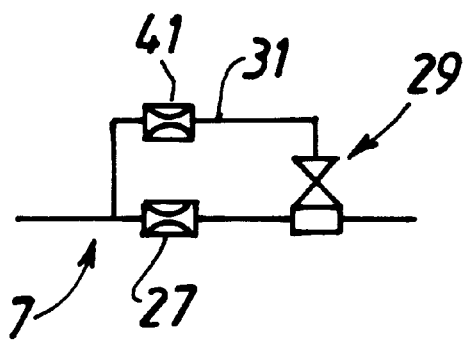
Figure 5C:
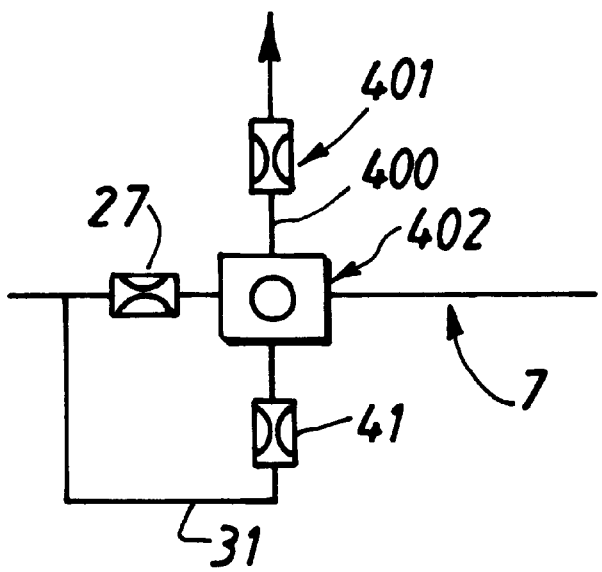
Figure 6:
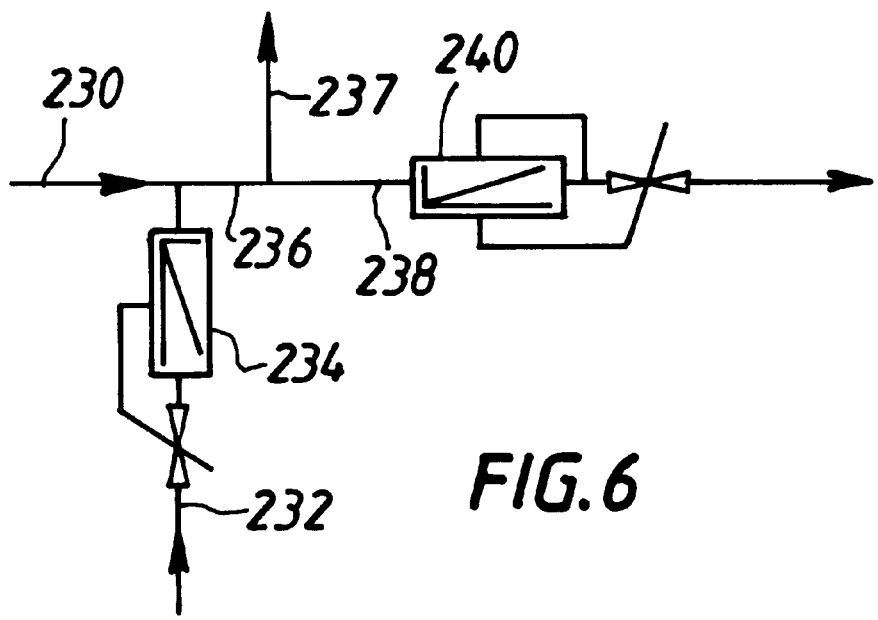
FIG. 6 is a diagram of a dilution stage.

FIGS. 5A, 5B and 5C illustrate other embodiments of the regulating devices 14A and 14B.

The first two embodiments employ a valve of the branching valve type, the last embodiment (FIG. 5C) employing a valve of the "4-way" type.

Thus, considering the example in the FIG. 5A, the valve 29, which is a branching valve, lies at the upstream point of connection of the bypass line 31 to the feed line 7, the first calibrated restriction 27, lying on the feed line portion between the valve and the downstream point of connection of the bypass line, therefore lying downstream of this valve.

As regards FIG. 5B, this illustrates a case in which the branching valve 29 lies at the downstream point of connection of the bypass line 31 to the feed line 7, the first calibrated restriction 27, lying on the main line portion between the upstream point of connection of the bypass line and the valve, therefore lying upstream of this valve.

As indicated earlier, although FIGS. 5A and 5B illustrate embodiments which employ only one branching valve, according to other embodiments of the invention it would also be possible to place two branching valves, one at the upstream point of connection and one at the downstream point of connection of the bypass line to the main line.

FIG. 5C illustrates a case in which a 4-way valve 402 is used, said valve here lying at the down-stream point of connection of the bypass line 31 to the feed line 7, the first calibrated restriction 27 lying upstream of this valve.

It will be noted that this figure illustrates an advantageous embodiment of the invention in which, on a fourth way 400, which may be termed a "leakage way", is placed an additional calibrated restriction (the diameter of which is much smaller than that of the restrictions 27 and 41) making it possible to maintain a small leakage flow in this line, for example one lying within the range 1 to 100 cm$^3$/min.

The operation of this configuration (which is characterized in that in none of the branches is there no flow) may therefore be described in the following manner:

when the valve is closed, the flow rate in the main line is limited by the restriction 27 while the flow rate in the line 31/400 is limited by the two restrictions in series, 41 and 401, and therefore in practice essentially by the restriction 401;

when the valve is open, the two "perpendicular" ways are brought into communication with each other, the flow rate in the main line 7 then being the sum of the flow rates flowing through the restriction 27 and the restriction 41, knowing that in this calculation it is necessary to subtract the very small leakage flow rate through the orifice 401.

II. Device for delivering a pure gas charged with a predetermined quantity of gaseous impurities The various units of the device 9 for delivering a pure gas charged with a predetermined quanity of gaseous impurities, namely the purification unit 17, the source of impurities and the means 16 of diluting the impurities in the pure gas in a predetermined manner, are presented in detail hereinbelow.

II.1. Purification unit

II.1.1. Structure of the purification unit

The purification unit 17 comprises an inlet line 160 and a line 162 for delivering a pure gas, between which are placed in parallel three purifiers 164, 166, 168, such as, for example, a nitrogen purifier, a hydrogen purifier and an argon purifier.

The inlet of each purifier is joined via a branching valve 170, 172, 174 to the inlet line 160. The outlet of each purifier 164, 166, 168 is connected to the delivery line 162 of the purification unit 17 by means of a valve 176, 178, 180 for supplying the circuit with the purified gas.

The valves 170 to 180 are identical to the valves 29 of the regulating devices 14A, 14B.

Thus, each branching valve 170, 172, 174, as well as each valve 176, 178, 180 for supplying the circuit with the purified gas, comprises a first conduit 33 permanently connected at one end to a corresponding purifier 164, 166, 168. The second conduits 35 of the branching valves 170, 172, 174 are placed in the inlet line 160. The second conduits 35 of the valves 176, 178, 180 for supplying the circuit with the pure gas are placed in the delivery line 162.

The feed line 160 is connected, downstream of the valve 174, to a purge line 182 in which an element 184 for creating a pressure drop, such as a calibrated orifice, is placed.

The outlet line 162 is connected, at the end opposite the diluting means 16, to an associated purge line 186 in which an element for creating a pressure drop 188, such as a calibrated orifice, is placed.

The purge lines 182 and 186 come together into a common purge line 190 downstream of the calibrated orifices 184 and 188.

II.1.2. Operation of the purification unit

Depending on the kind of gas which is output by the source 5, the inlet valve 170 of the purifier 164 associated with this gas and the valve 176 of the corresponding outlet are, for example, switched to the state for bringing the conduits 33 and 35 into communication with each other. The gas to be analyzed from the source 5 flows freely through the purifier 164, which purifies this gas. The other valves 172, 174, 178 and 180 are in the isolating state.

If the nature of the gas output by the pressure source 5 is changed, the valves 170, 176, which hitherto were open, are switched to the isolating state and the valves associated with another purifier are switched to the communicating state.

By virtue of the construction of the valves 170 to 180 and by virtue of the restrictions allowing a leakage flow, the feed line 160 and the outlet line 162 are continuously purged. This purification unit 23 furthermore has the advantage that it can be used with various kinds of gases to be purified and that it is virtually free of flow-stagnation volumes.

Advantageously, in order to switch the valves, diaphragm valves are used which include means for controlling the switching of the actuator between the communicating and isolating positions, such as pneumatic or electromagnetically-operated valves for example. The means for controlling the movement for the actuator of each valve are connected to a control unit, such as a microcomputer or a logic controller for example. This control unit includes switching logic means. These logic means are produced, for example, by a computer program loaded into the microcomputer which excludes the possibility of two purifiers being simultaneously in communication with the feed line 160 and the outlet line 162.

II.2. The source of impurities

The source of impurities 15 comprises a reservoir containing a mixture of various kinds of gases such as, for example, $N_2$, $CO_2$, CO, $O_2$, $CH_4$, $H_2$, Ar, Kr, Xe, He, etc. This mixture has been produced in such a way that the volume concentrations of most of the gases in this mixture are of the same order of magnitude.

For safety reasons, the concentration of an inert gas, such as helium for example, is chosen to be much higher than the volume concentration of all the other constituents of the mixture. By virtue of such a composition of the mixture, oxidants, such as $O_2$ or CO, may coexist together with fuels, such as $CH_4$, for example, without their being a risk of the reservoir 15 catching fire or exploding.

In order to know accurately, after dilution, the contents of the trace impurities in the pure gas, the composition of the mixture in the reservoir 15 has been accurately determined beforehand using gas analysis means, such as a gas chromatograph for example. The reservoir 15 may, for example, be a bottle under a high pressure (typically 200 bar).

The gases in the mixture are sampled or introduced into the diluting means 16 via a sampling line 204 into which a downstream pressure regulator 205 is placed. The sampling line 204 emerges in an associated purge line 206 in which a shutoff valve 207 and an element for creating a pressure drop, such as a calibrated orifice 208, are placed.

II.3. The means of diluting the gaseous impurity in the pure gas in a predetermined manner The diluting means 16 comprise, on the one hand, the means 19 of splitting the flow of pure gas delivered by the feed line 162 at the outlet of the purification unit 17 and, on the other hand, three dilution stages 20, 21, 22 placed in series. A pressure gage 86 is placed in the line 162 upstream of the splitting means.

The splitting means 19 comprise the regulating device 14B and two lines 209, 210, said regulating device and said lines being connected in parallel with the feed line 162. A calibrated restriction 211, 212, such as a calibrated orifice, is placed in each line 209, 210.

The line from the regulating device 14B as well as the lines 209 and 210 with their respective orifices 211, 212 each form a branch for feeding a corresponding dilution stage 20, 21, 22, with pure gas.

The operation of such flow-splitting means is described in detail in document FR-A-2714968 in the name of the Applicant Company. This is why this operation will not be described hereinbelow.

FIG. 5 shows an example of a dilution stage 20, 21 or 22. A dilution stage 20, 21 or 22 comprises a pure gas feed line 230, connected to a corresponding branch of the splitting means 19, and an impurity-containing gas feed line 232.

A mass flow regulator 234 is placed in the feed line 232 so as to enable the degree of dilution of the dilution stage to be varied.

The feed lines 230 and 232 are joined together in such a way that they emerge in a common mixing line 236. The line 236 emerges, on the one hand, in an outlet 237 of the dilution stage. This outlet line 237 is connected to the feed line 232 of the dilution stage placed just downstream.

On the other hand, in the case of the dilution stages and 21, the dilution line 236 is connected to a purge line 238 in which a diverter 240 is placed. The pressure of a diverter in one dilution stage is set in such a way that, on the one hand, and preferably, the sonic conditions for the diluting means are satisfied and, on the other hand, the pressure set is slightly higher than the pressure set in the diverter placed in a dilution stage downstream, so as to ensure that the gases flow toward the analyzer 3.

The feed line 232 of the dilution stage 20 is joined, downstream of the pressure regulator 205 and upstream of the shutoff valve 207, to the sampling line 204.

The outlet line 237 of the final dilution stage 22 emerges in the outlet line 10 of the delivery device 9, downstream of the regulating device 14B.

The flows at the inlet of each dilution stage are set in such a way that a dilution of approximately 1/1000 of the gas output by the line 232 in the pure gas output by the line 230 is obtained.

Of course, the "zero" impurity quantity is also a predetermined quantity of trace impurities which the device has to deliver to the analyzer 3. This is why the feed line 232 of the final dilution stage 22 includes a bypass line 242 in which a mass flow regulator 244 is placed.

The outlet line 10 of the delivery device 9 outputs a pure gas in the case in which the regulator 244 is set to a flow rate greater than that of the regulator 234 of the dilution stage 22 and it outputs a pure gas charged with a predetermined quantity of trace impurities in the case in which the flow rate controlled by the regulator 244 is less than that of the regulator 234.

The impurity $H_2O$ is generated here by a permeation cartridge 250 outputting approximately 250 ng/min and connected as a branch off the pure gas line 230 of the second dilution stage 21.

This permeation cartridge contains water heated to 50 C. and includes, at one end, a silicone membrane through which the $H_2O$ molecule diffuses.

It will be noted that the cartridge could be placed on the first stage for a higher permeation rate, the permeation rate being chosen to generate in the line a content equivalent to that of the gaseous impurities present at this level of dilution.

Table 1 below shows, for a predetermined composition of the gas mixture in the reservoir 15, two examples of manufacture of a pure gas charged with a predetermined quantity of trace impurities which is output by the outlet line 10 of the delivery device 9, these examples being made in one case with hydrogen as the pure gas and in one case with nitrogen as the pure gas.

TABLE 1

| Impurities | Composition of the reservoir in vol. % | Concentration of the impurities, $H_2$ pure gas | Concentration of the impurities, $N_2$ pure gas |
| --- | --- | --- | --- |
| $O_2$ | 5% | 0.20 ppb | 1.62 ppb |
| $H_2$ | 5% | — | 1.62 ppb |
| $N_2$ | 5% | 0.20 ppb | — |
| Ar | 5% | 0.20 ppb | 1.62 ppb |
| CO | 5% | 0.20 ppb | 1.62 ppb |
| $CO_2$ | 5% | 0.20 ppb | 1.62 ppb |
| $CH_4$ | 5% | 0.20 ppb | 1.62 ppb |
| Xe | 5% | 0.20 ppb | 1.62 ppb |
| Kr | 5% | 0.20 ppb | 1.62 ppb |
| He | 55% | 2.19 ppb | 17.85 ppb |
| $H_2O$ | permeation cartridge | 0.81 ppb | 1.58 ppb |

By virtue of the fact that the initial composition of the reservoir 15 has been accurately determined beforehand and that these impurities are diluted in a very precise manner, a pure gas containing a precisely known concentration of trace impurities is obtained.

In addition, using the flowmeters 234 in the feed line 232 of each dilution stage 20, 21, 22, it is possible to vary the range of concentrations of the trace impurities by a factor of 100.

By virtue of the fact that the reservoir 15 contains a mixture of several gases, this constitutes trace impurities in various pure gases. Together with the purification unit 17, the generation of a pure gas charged with predetermined quantities of given trace impurities is therefore considerably facilitated by this device.

III. Device for selecting one of the two gases

As has already been described, the device 13 for selecting one of the two gases comprises two feed lines 11, 12, one of which, 11, is connected to the analyzing line 7 and the other, 12, to the outlet line 10 of the delivery device 9.

Each feed line 11, 12 emerges in a respective purge line 300 and 302. The feed lines 11 and 12 are connected together by means of a connecting line 304. The connecting line 304 is connected to the analyzer 3 via a gas delivery line 306. The outlet of the analyzer 3 also emerges in an associated purge line 308. The purge lines 300 and 308 each include a mass flow regulator 310, 312. A diverter 314 is placed in the purge line 302.

In order to deliver the gas contained in the line 11 to the analyzer 3, the sum of the flow rates $D_{310}+D_{312}$ controlled by the flow regulators 310 and 312 is set to a flow rate which is less than the flow rate $D_{11}$ of the flow output by the line 11. In order to deliver a calibration gas, that is to say either a pure gas or a gas charged with a predetermined quantity of impurities, to the analyzer 3, the flow rate $D_{310}$ of the flow regulator 310 is set so that it is greater than the flow rate $D_{11}$ of the flow coming from the line 11, and the flow rate $D_{312}$ controlled by the regulator 312 is set so that it is slightly less than the gas flow rate $D_{12}$ in the line 12. The pressure of the gas introduced into the analyzer 3 is controlled by the diverter 314 placed in the purge line 302.

Advantageously, by means, of such an arrangement, it is possible not only to select, for delivery to the analyzer 3, the gas to be analyzed or the calibration gas, but it is also possible to control parameters relating to the introduction of the gases into the analyzer 3, such as the flow rate and the pressure.

By virtue of the fact that a smaller number of regulating components is used compared with the device described in the French Patent Application FR-A-2714968, the cost of the plant is considerably reduced. In addition, a reduction in the number of regulating components also means that there is an increase in the accuracy and reliability of the apparatus 3.

We claim:

1. A device for regulating the flow of gases having substantially different molar masses, comprising
    a feed line connected to a gas source at a defined pressure and to an apparatus,
    a first nonvariable calibrated restriction placed in the feed line, the first restriction defining an opening smaller in area than an area of the feed line,
    a bypass line connected via at least one of its two ends to a valve, placed in the feed line, and via the other cad to a point of connection to the feed line, said valve being switchable between a first position for bringing the feed line into communication with the bypass line and a second position for isolating the bypass line from the feed line, and
    a second nonvariable calibrated restriction placed in the bypass line, the second restriction defining an opening smaller in area than an area of the bypass line, the first calibrated restriction being placed on the feed line portion lying between the valve and the point of connection,
    wherein a size of the second calibrated restriction relative to a size of the first calibrated restriction is selected such that a first gas having a first molar mass and a second gas having a second molar mass different from the first molar mass have essentially the same volume flow rates through the device when only the first gas flows through the feed line and the first calibrated restriction at a particular temperature and a particular pressure and when only the second gas glows through the feed line and the first calibrated restriction and the bypass line and the second calibrated restriction at the particular temperature and pressure.

2. The device according to claim 1 comprising two branching valves lying respectively at an upstream point of connection and at a downstream point of connection of the bypass line to the feed line.

3. The device according to claim 1 wherein the valve used is a branching valve lying at an upstream point of connection of the bypass line to the feed line, the first calibrated restriction being placed on a portion of the feed line lying between the valve and a downstream point of connection of the bypass line, downstream of the valve.

4. The device according to claim 1 wherein the valve used is a branching valve lying at a downstream point of connection of the bypass line to the feed line, the first calibrated restriction being placed on a portion of the feed line lying between an upstream point of connection of the bypass line and the valve, upstream of the valve.

5. The device according to claim 1 wherein the valve used is a 4-way valve, lying at a downstream point of connection of the bypass line to the feed line, the first calibrated restriction being located on a portion of the feed line lying between an upstream point of connection of the bypass line and the valve, upstream of this valve.

6. The device according to claim 5 wherein the four way valve includes a fourth way onto which has been placed an additional calibrated restriction, the diameter of which is smaller than that of the first and second restrictions, capable of permanently maintaining a small leakage flow in this fourth way.

7. The device according to claim 1, wherein the second calibrated restriction is disposed proximate a downstream end of the bypass line.

8. The device according to claim 1 wherein the calibrated restrictions are calibrated orifices.

9. The device according to claim 1 wherein the branching valve comprises
    a first conduit having first and second ends, the first conduit being permanently connected via the first end to the bypass line,
    a second conduit placed in the feed line, and
    an actuator which can be switched between a position for bringing the first conduit into communication with the second conduit and a position for isolating the first conduit from the second conduit, the second conduit being free of flow-stagnation volumes.

10. The device according to claim 9, wherein the second conduit of the valve includes a chamber in which the second end of the first conduit emerges and the valve includes a closure element which is acted upon by the actuator of the valve, which closure element closes off, in said isolating position, the end of the first conduit emerging in said chamber and which is set back with respect to this end of the first conduit in said communicating position.

11. The device according to claim 10 wherein the end of the first conduit emerging in said chamber is provided with a seal projecting into the chamber and the closure element comprises an elastically deformable diaphragm forming part of the wall of the chamber opposite the seal, the diaphragm being pressed in a sealed manner onto the seal against the spring force of the diaphragm, in said isolating position, by a pusher of the actuator.

12. Device according to claim 9, wherein the valve includes means for controlling the switching of the actuator between said communicating and isolating positions.

13. Device according to claim 1, wherein the valve is a branching-type valve.

14. Device according to claim 1, wherein the valve is a four-way-type valve.

* * * * *